United States Patent [19]
Israel

[11] Patent Number: 6,013,101
[45] Date of Patent: Jan. 11, 2000

[54] ACCOMMODATING INTRAOCULAR LENS IMPLANT

[75] Inventor: Henry M. Israel, Bnei Brak, Israel

[73] Assignee: Acuity (Israel) Limited, Bnei Brak, Israel

[21] Appl. No.: 08/776,713

[22] PCT Filed: Nov. 21, 1995

[86] PCT No.: PCT/US95/14555

§ 371 Date: Apr. 28, 1997

§ 102(e) Date: Apr. 28, 1997

[87] PCT Pub. No.: WO96/15734

PCT Pub. Date: May 30, 1996

[30] Foreign Application Priority Data

Nov. 21, 1994 [IL] Israel ..................................... 111713

[51] Int. Cl.[7] ................................................ A61F 2/16
[52] U.S. Cl. ................................................ 623/6
[58] Field of Search ................................................ 623/6

[56] References Cited

U.S. PATENT DOCUMENTS

| | | | |
|---|---|---|---|
| Re. 34,998 | 7/1995 | Langerman | 623/6 |
| 4,253,199 | 3/1981 | Banko | 623/6 |
| 4,254,509 | 3/1981 | Tennant | 623/6 |
| 4,409,691 | 10/1983 | Levy | 623/6 |
| 4,426,741 | 1/1984 | Bittner | 623/6 |
| 4,463,458 | 8/1984 | Seidner | 623/6 |
| 4,575,373 | 3/1986 | Johnson | 623/6 |
| 4,790,847 | 12/1988 | Woods | 623/6 |
| 4,842,601 | 6/1989 | Smith | 623/6 |
| 4,888,012 | 12/1989 | Horn et al. | 623/6 |
| 4,892,543 | 1/1990 | Turley | 623/6 |
| 4,902,293 | 2/1990 | Feaster | 623/6 |
| 4,963,148 | 10/1990 | Sulc et al. | 623/6 |
| 4,994,082 | 2/1991 | Richards et al. | 623/6 |
| 5,047,051 | 9/1991 | Cumming | 623/6 |
| 5,108,429 | 4/1992 | Wiley | 623/6 |
| 5,152,789 | 10/1992 | Willis | 623/6 |
| 5,275,623 | 1/1994 | Sarfarzai | 623/6 |
| 5,275,624 | 1/1994 | Hara et al. | 623/6 |
| 5,476,514 | 12/1995 | Cumming | 623/6 |
| 5,496,366 | 3/1996 | Cumming | 623/6 |
| 5,593,436 | 1/1997 | Langerman | 623/6 |
| 5,674,282 | 10/1997 | Cumming | 623/6 |

FOREIGN PATENT DOCUMENTS

| | | |
|---|---|---|
| 0337390 | 10/1989 | European Pat. Off. . |
| 0507292 | 10/1992 | European Pat. Off. . |
| 0592813 | 4/1994 | European Pat. Off. . |

OTHER PUBLICATIONS

Schachar, "Cause and Treatment of Presbyopia with a Method for Increasing the Amplitude of Accommondation", Ann. Ophthalmol. 1992;24:445–452.

Schachar, Ann. Ophthal., 1993; 25:404–409.

Schachar, Ann. Ophthal., 1994; 26:4–9.

Koretz et al., "How the Human Eye Focuses", Scientific American, Jul. 1988, pp. 64–71.

Grinberg, "Questioning Our Classical Understanding of Accommodation and Presbyopia", American Journal of Optometry & Physiological Optics, vol. 63, No. 7, pp. 571–580.

International Search Report and Annex.

International Preliminary Examinaton Report.

*Primary Examiner*—David H. Willse
*Attorney, Agent, or Firm*—Greenblum & Bernstein, P.L.C.

[57] ABSTRACT

An intraocular lens assembly for implantation in a human eye, the eye including a ciliary muscle and zonules controlled by the ciliary muscle, the assembly including an optic having anterior and posterior surfaces depending from a common edge, at least two, preferably rigid, linkage arms, each being attached to the optic at a first position on the arm thereof and cooperating with ciliary muscle or the zonules at a second position on the arm, and at least two pivots, one of which is rotatably attached to each respective linkage arm intermediate the first and second positions.

14 Claims, 13 Drawing Sheets

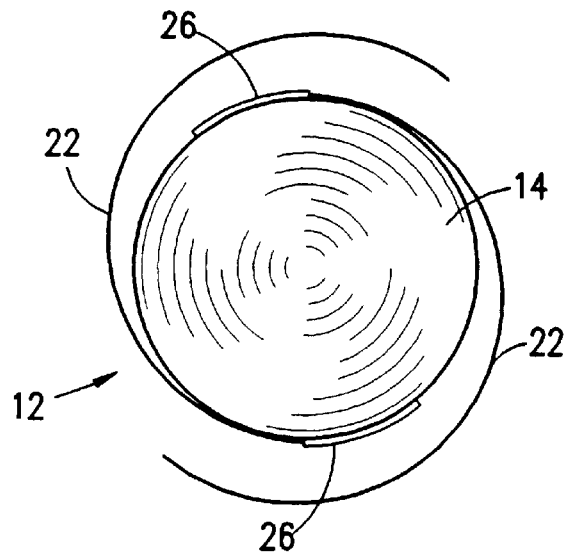
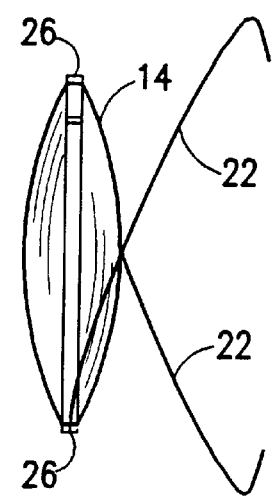
FIG. 2A    FIG. 2B
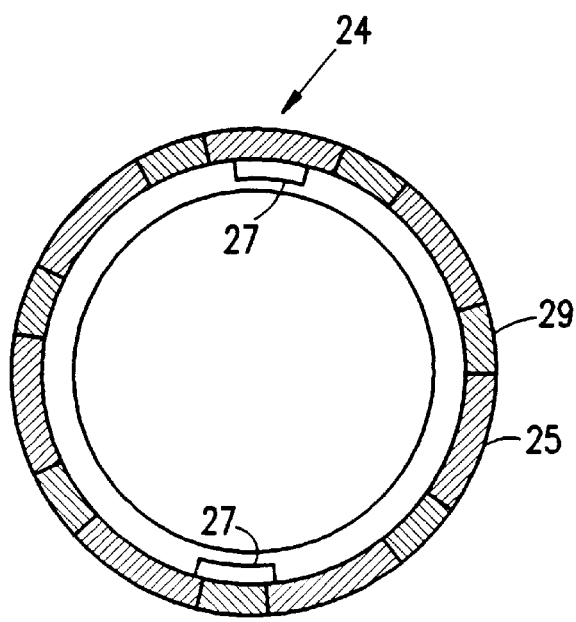
FIG. 3

ACCOMMODATING INTRAOCULAR LENS IMPLANT

FIELD OF THE INVENTION

This invention relates to an intraocular lens assembly, for implantation into the human eye, which permits accommodation in response to the contraction and relaxation of the ciliary muscles.

BACKGROUND OF THE INVENTION

Normally when a person focuses on an object disposed at a distance from the eye, focusing is achieved by virtue of the contraction of the ciliary muscles which affects the curvature of the lens and thereby its focal length. The process whereby the eye is able to focus on objects over a wide range of distances from the eye is called "accommodation". It is known, during cataract operations, for example, to remove material from the lens capsule and replace it by an intraocular lens implant. The simplest of such implants are fixed lenses having a single focal length. Such lenses do not provide for any accommodation by the eye for the distance of objects and therefore are of relatively limited utility.

An improved type of lens for implantation provides a number of focal lengths. Some of the light impinging the lens is subjected to focusing at each of the different focal lengths of the lens. This type of lens does provide for a broader range of focus for the eye. Only a portion of the light, however, is focused on the retina of the eye for any of the focal lengths. Thus, if an object is focused by one of the focal lengths, only 25–50% of the light will be focused, the remainder will be only partly focused or unfocused. This results in a reduction of contrast of the focused object and a reduction in visual acuity.

A number of proposals have been made for changing the focal length of the lens in response to the natural accommodation mechanism of the eye. While these adaptive lens proposals exist on paper, none of them are commercially available and, as far as is known to the applicant, none have been reported as having been implemented in humans.

One type of adaptive lens comprises an artificial lens whose shape is changed in response to the contraction and expansion of the ciliary muscle. This type of lens is proposed in U.S. Pat. Nos. 4,842,601 to Smith, 4,888,012 to Horn et al. and 4,253,199 to Banko.

Two other types of adaptive lenses are described in U.S. Pat. No. 4,994,082 to Richards et al. Some embodiments described in this patent comprises one or two lenses whose position in the plane perpendicular to optic axis of the eye is adjusted by a mechanical structure effected by the ciliary muscle of the eye. A second type of embodiment utilizes two lenses (comprising a compound lens) whose spacing along the optical axis is adjusted to change the focal power of the compound lens. U.S. Pat. No. 5,275,623 to Sarfarazi show a similar type of compound adaptive lens. U.S. Pat. No. 4,892,543 to Turley describes a compound system comprising a fixed lens having curved posterior and anterior surfaces and a second component which is positioned axially posterior of the lens. During accommodation, the movable component is forced against the posterior surface of the lens. The movement and subsequent distortion of the movable portion results in a change in the focal power of the compound lens.

U.S. Pat. Nos. 4,790,847 to Woods, 5,152,789 to Willis, 4,409,691 to Levy and 4,254,509 to Tennant describe adaptive lens systems utilizing a simple intraocular lens. These systems have focusing capabilities which are achieved by axially shifting the lens in response to normal contraction and expansion of the ciliary muscle resulting from changes in range between the eye and an object under observation. These patents (and the Turley and Richards et al. patents) describe similar systems for providing motion of the lens. In each case the ciliary muscle controls zonules, which in turn provide tension to a lens capsule in which the lens system is mounted. The extremities of the capsule press against a radially compelled, spring-like structure which also forms a relatively large angle of somewhat less than 90° with the optical axis of the eye. The lens is positioned on the optical axis. Relaxation of the ciliary muscle releases the radial force and allows the spring to form a more nearly flat shape. When the ciliary muscle contracts, the pressure on the spring is increased by the action of the lens capsule, the angle between the spring and the optical axis is decreased, and the lens moves axially away from the ciliary muscle. This causes an increase of the offset of the lens from the plane of the ciliary muscle. The movement of the lens changes the position of the lens vis-a-vis the retina resulting in accommodation of the eye for the distance of a viewed object.

The bias of the lens with respect to the eye is different for the various patents, with Tennant, Willis, Turley and Levy having the lens biased toward the posterior of the eye and Woods having the lens biased toward the anterior of the eye.

The theory on which Woods bases his approach is that of the classical Helmholtz hypothesis of accommodation, in accordance with which when the eye is focused for far vision, the ciliary muscle relaxes and the lens capsule assumes a more discoid shape. This occurs because the extremities of the lens capsule are attached via the zonular fibers to the ciliary muscle. According to Helmholtz, contraction of the ciliary muscle reduces tension in the zonular fibers whilst relaxation of the ciliary muscle has the reverse effect.

In the Woods patent the system includes an optic (lens) and at least two rearwardly extending haptics which bear against the circumference of the lens capsule and are so formed that the lens bears against the anterior wall of the lens cavity when the ciliary muscle is contracted, thus adjusting for correct near vision.

Woods provides a very detailed resume of the relevant prior art and, rather than describe the techniques which have been used for intraocular implant, the reader is referred to the Woods patent which is incorporated herein by reference.

U.S. Pat. No. 4,409,691 to Levy is also based on the Helmholtz model but uses a different arrangement to provide accommodation. In Levy, the optic is provided with a pair of radially extending struts which are molded integrally with the optic and are just long enough so that their respective terminations are in light pressure contact with the perimeter of the lens capsule when the optic is implanted in the eye, the ciliary muscle then being relaxed. The optic itself bears against the posterior cavity wall and provides correct focus for far vision.

In Levy the capsule is controlled by the ciliary muscle itself and not by the zonules, which may, in fact, be removed and replace by a soft cushion in one of his embodiments. In accordance with the Helmholtz hypothesis, the ciliary muscle contracts as the eye tries to focus on a nearby object, it drives the outer end of the struts radially inwardly, thereby forcing the optic forwardly, away from the fovea centralis and increasing the optic-to-image distance. This allows the eye to focus on relatively near objects.

When the eye tries to focus again on far objects, the ciliary muscle relaxes, the extremities of the lens capsule move radially outward and the compressive force bearing on the struts is reduced, allowing the optic to move further back toward the posterior cavity wall.

Both Woods and Levy are based on the same principle, namely the movement of the lens away from the fovea during accommodation when the ciliary muscle contracts. In Woods, the haptics are constructed such that the contraction of the ciliary muscle causes the lens to be forced against the anterior wall of the lens capsule while in Levy the struts are so constructed that the lens is moved away from the fovea by the posterior wall of the lens capsule.

Recent research, however, indicates that the Helmholtz hypothesis of accommodation for near vision may be incorrect. Specifically, Ronald A. Schachar reports in Ann. Ophthal. 1992; 24:445–452 that, during accommodation, contraction of the ciliary results in an increase in zonular tension. Thus, according to Schachar, "the equatorial diameter of the lens is actually increased in contrast to Helmholtz's hypothesis and its modifications. When the ciliary muscle contracts during accommodation, the peripheral volume of the lens is decreased, resulting in an increase in the central volume of the lens and the optical power of the lens". This conclusion is reiterated by Schachar in Ann. Ophthal. 1993; 25:404–409 wherein he states: "Helmholtz's hypothesis of accommodation and its modifications state that the equatorial diameter of the lens decreases during accommodation. In contradiction, Schachar's hypothesis asserts that the equatorial diameter of the lens increases with accommodation."

Further research by Schachar, Ann. Ophthal. 1994; 26:4–9 corroborates his hypothesis.

Consequently, the theory in accordance with which the Woods patent is based, namely the change in tension of the zonules with accommodation, may be incorrect and the device of Woods, if one were to install it in a patient, could give reverse accommodation.

One problem which occurs with the implantation of accommodating lenses having a fixed focal length relates to the need to provide sufficient axial displacement of the optic within the eye in order to provide correct focusing throughout the complete range from near to far vision. It will be understood that the ciliary muscles themselves undergo a maximum radial displacement of approximately 200 micrometers from their relaxed to contracted conditions. Additionally, for a fixed focal length optic, an axial displacement of approximately 1 mm is necessary to allow for complete accommodation. In other words, the very slight radial displacement of the ciliary muscle must be amplified in order to allow for complete accommodation.

Prior art patents attempt to achieve this amplification of movement by providing haptics (or struts or other coupling elements) which form a relatively large angle with the optic axis. Th small radial movements of the ciliary muscle are translated into much larger movements in the direction of the optical axis. This amplification is approximately equal to the tangent of the angle with the optical axis. This amplification is reduced, however, by inherent flexibility of the coupling elements. Moreover, such amplification is very sensitive to the angle of the elements with the optical axis, which angle itself varies with the amount of accommodation and is not well controlled.

Furthermore, no surgical adjustment is made in the prior art references for locating the intraocular lens implant at precisely the correct distance from the retina to allow for correct far or near vision. Thus, both Woods and Levy who design their optics for correct far vision, merely assume that the ciliary muscle is relaxed (as required by Helmholtz's hypothesis) and design the haptics (or struts) and optic so that the optic is of proper strength and is properly positioned to achieve focus for distant objects when the eye is relaxed.

However, it would clearly be desirable to provide an intraocular lens implant allowing for complete accommodation and also permitting surgical adjustment so that the eye is correctly focused without the need for correction spectacles.

U.S. Pat. No. 4,575,373 to Johnson describes a non-accommodating (i.e., non-adaptive) lens whose shape may be adjusted using an external laser which selectively heats a portion of the periphery of the lens and causes the shape of the lens to change. This causes a permanent change in the focal power of the implanted lens. However, there is no teaching of how such an adjustable lens may also be made adaptive.

SUMMARY OF THE INVENTION

The present invention provides an improved method and apparatus for providing accommodation utilizing one or more optics which move in response to changes in the ciliary muscle and the zonules.

These improved methods are generally characterized by improved control over the motion of the optic and/or increased axial movement of the optic for a given change in the tension in the ciliary muscle and the zonules.

In some embodiments of the invention this improvement is achieved by utilizing rigid haptics or linkage arms rather than resilient haptics. In other embodiments of the invention this improvement is achieved by utilizing a fulcrum and pivot structure for the haptics which act as lever arms or linkages. Some embodiments of the invention include both these improvements.

Within the context of the invention the terms "rigid" and "flexible" or "resilient" have a special meaning. The haptics attached to the optic in prior art, such as in the Woods patent, to which reference has been made, are, in fact, resilient wires formed of plastics or any other biologically inert material. They are sufficiently stiff so that when a compressive force is applied thereto, they distort but do not buckle. Rather, they push the optic to which they are attached forward along the optical axis. However, they are also sufficiently resilient so that when the compressive force is reduced, they spring back under their own elasticity so as to return the optic toward its original position. It is this property, namely that a compressive force applied to the lever arms does not cause them to buckle or otherwise collapse, which is essential for prior art inventions, and it is to this extent that the term "flexible, resilient" is to be understood herein.

Many preferred embodiments of the present invention, however, use substantially rigid elements, and in particular substantially rigid linkage arms or haptics. These elements are considered to be rigid because, in these embodiments, they do not deform significantly under the compressive or tensile forces present during accommodation. They are, therefore, capable of transmitting forces applied to them more efficiently than flexible elements and potentially with greater mechanical advantage. It is in this context that the term "rigid" is to be understood in relation to the present invention. It should be understood, however, that these "rigid" segments are made of very thin material and may not be rigid under other circumstances, such as during surgical implantation, when greater force is applied to them so that they can be inserted into the lens capsule.

Other preferred embodiments of the present invention, however, may use linkage arms or haptics made of flexible, resilient material, which may be similar to the haptic materials used in Woods and other prior art patents. Preferred embodiments of the present invention using flexible, resilient linkage arms still differ from the prior art, however, by virtue of their use of pivot connections to convert radial motion of the ciliary muscle and zonules to axial motion of the optic more efficiently and with greater mechanical advantage.

The present invention also provides, in some embodiments thereof for improved haptic configurations, improved methods of attachment of haptics to the optic and for improved methods of providing structure to the lens capsule remaining after surgery to further increase the effectiveness of the accommodation of the eye after lens replacement.

In yet another aspect of the invention, method and apparatus are provided for adjusting the position of the optic during or after its implantation so as to provide optimum accommodation.

Furthermore, embodiments of the present invention can be designed to operate properly in the eye regardless of whether the classical Helmholtz theory or the new Schachar theory of accommodation is correct.

In one group of embodiments of the present invention, an intraocular lens assembly incorporates an optic for implantation within the lens capsule of the eye, the optic being held in place by at least two substantially rigid linkage arms, or haptics, which are attached at their inner ends to the edge or face of the optic. The outer ends of the linkage arms are coupled with the movement of the zonules and the ciliary muscle. The optic, linkage arms and connecting parts are made of biologically inert plastic or other biologically inert materials.

In this group of embodiments, the linkage arms are connected to pivot joints at one or both the inner and outer ends thereof, which permit the arms to rotate about the pivot axes in response to radial expansion or contraction of the equatorial diameter of the capsule. When the ciliary muscle of the eye is relaxed, for distance vision, the arms hold the optic in a position which focuses distant images onto the retina. When the ciliary muscle contracts to accommodate for near vision, the equatorial diameter of the lens capsule changes, exerting force on the outer ends of the linkage arms and thereby causing them to rotate about their pivots and shift the optic forward, away from the retina, so as to focus near images onto the retina. When the ciliary muscle again relaxes, the linkage arms move in the opposite direction, returning the optic to its previous position of distant focus.

It may be appreciated that the equatorial diameter of the lens capsule is determined at any time by the balance of outward radial force exerted by the zonular fibers and inward force due to the natural elasticity of the lens capsule. Furthermore, the portions of the lens capsule remaining after surgery, particularly the posterior wall of the lens capsule, provide, in some embodiments of the invention, a force which (axially) biases the optic toward the front of the eye. Further embodiments of the invention provide other elements for exerting forces which may affect the balance of forces acting on the optic and change its axial position.

In some preferred embodiments of the present invention, the outer-ends of the linkage arms are held in contact with or attached to an expanding ring, which is itself in contact with the edges of the lens capsule adjacent to the zonules. The expanding ring serves both to hold the capsule open (i.e., to prevent is axial collapse) and to couple the linkage arms to the motion of the zonules. This expanding ring may also exert an additional outward radial force on the equatorial edge of the capsule or may be segmented so that it provides only to position the linkage arms and to hold the lens capsule open.

Further embodiments of the invention incorporate two or more springs or other tensile members attached at one of their respective ends to the ciliary muscle, zonules or expanding ring at symmetrically spaced points surrounding the capsule of the eye. The other ends of the springs are either fastened together centrally or attached to the ciliary muscle, zonules or expanding ring in such a way as to cause an inward radial force to be exerted on the equatorial edge of the capsule. For example, such tensile members may take the form of a tensioned ring attached along the periphery of the lens capsule. This type of tensile member effectively reinforces the inherent tension of the edge of the lens capsule itself. Such tensioned members are especially useful when the posterior wall of the lens capsule is also removed.

The ciliary muscle or zonules produce a contrary force, in the outward axial direction. Outward radial motion of the zonules or ciliary muscle will stretch the springs, increasing the forward axial force and causing the optic to move forward in the capsule. When the zonules or ciliary muscle subsequently return radially inward, the linkage arms will force the optic back to its previous position.

In general, the lens capsule itself performs a similar function, in a somewhat different way. The elasticity of the capsule, especially when the capsule is held open by the expanding ring, exerts an inward force on the edge of the lens capsule, where it is attached to the zonules. The posterior wall of the lens capsule performs an additional function in many embodiment of the invention, in that in these embodiments the optic is in contact with the posterior wall of the lens capsule. Under this condition, the posterior wall acts on the optic to provide a restoring force for the optic when the diameter of the lens capsule increases. In this way it is not necessary to attach the outer edge of the haptics to the expanding ring to provide movement of the optic when the diameter of the lens capsule is increased.

In a preferred embodiment of the invention, in accordance with Schachar's theory of accommodation, the optic is positioned initially, for distant vision, in contact with the posterior wall of the capsule of the eye. Two or more linkage arms, made of rigid plastic or other rigid material, are coupled flexibly to the optic so as to permit the linkage arms to pivot at the coupling during motion of the linkage arm, while still transmitting full axial motion from the arm to the optic. The outer ends of the linkage arms are likewise preferably flexibly attached to an expanding ring, which holds them in place at the edge of the capsule adjacent to the zonules.

According to Schachar's theory, when the eye accommodates for near vision, contraction of the zonules exerts an outward radial force, which causes the equatorial diameter of the lens capsule to increase. Consequent expansion of the expanding ring causes the arms to rotate in their respective pivot joints on the expanding ring and on the optic, thereby causing the optic to move axially forward in the capsule. The linkage arms are geometrically constructed in such a way that a small change in the equatorial diameter of the capsule will cause a larger change in optic position, sufficient to provide for focus of near images onto the retina.

An alternative preferred embodiment of the invention is similar to the embodiment described above, but is designed to operate in accordance with Helmholtz's theory. In this alternate embodiment the optic is coupled to the expanding ring by two or more linkage mechanisms, each of which comprises an inner arm and an outer arm. The inner arm is preferably rigidly connected at its inner end to the optic, and by a pivot at its outer end to the inner end of the outer arm. The outer arm is connected at its outer end to the expanding ring. When the ciliary muscle contracts for near vision accommodation, according the Helmholtz, the elasticity of the lens capsule causes the capsule's equatorial diameter to decrease and forces the expanding ring to contract. This contraction causes the outer arms to rotate about their pivots in such a way that the angle between the inner and outer arms at the pivot connecting them decreases. The inner and outer arms are so arranged that this rotation and decrease in pivot angle will cause the optic to move axially forward, thus providing for near images to be focused onto the retina.

The use of rigid linkage arms or haptics differentiates the above preferred embodiments and other alternative embodiments of this invention from prior art patents cited above, such as Woods and Levy. The aforementioned patents employ deformation of flexible wire haptics to convert radial motion of the ciliary muscle and zonules to axial motion of the optic. Some preferred embodiments of the present invention include rigid linkages, which do not substantially deform under the forces exerted by the ciliary muscle, zonules and lens capsule, and therefore transmit motion to the optic in a more efficient and reliable way.

Other preferred embodiments of the present invention, however, may use linkage arms or haptics made of flexible, resilient material, which may be similar to the haptic materials used in Woods and other prior art patents or may alternatively use rigid materials. The resilient materials are sufficiently stiff so that when a compressive force is applied thereto, they do not buckle, and when the compressive force is reduced, they spring back under their own elasticity to their previous shape. Preferred embodiments of the present invention using flexible, resilient linkage arms still differ from the prior art, however, by virtue of their use of pivot connections to convert radial motion of the ciliary muscle and zonules to axial motion of the optic more efficiently and with greater mechanical advantage.

In accordance with other preferred embodiments of the present invention, flexible, resilient linkage arms may be radially pre-loaded, for example by the pressure of the posterior wall of the lens capsule on the optic, so as to hold the intra-optic assembly in place without their connection to an expanding ring.

In other preferred embodiments of the invention, the outer ends of the linkage arms, whether rigid or flexible, may be fastened directly or indirectly to the zonules, ciliary muscle or radial edge of the lens capsule by suturing or gluing. It may be appreciated that the various types of mechanical linkages described here in relation to the various preferred embodiments of the invention may be used alternatively in conjunction with an expanding ring or with other methods, described herein, of coupling the linkage arms to the motion of the zonules or ciliary muscle.

In some preferred embodiments of the invention, the linkage arms or haptics are constructed of either rigid or resilient material, and are coupled to the edge of the capsule adjacent to the zonules, preferably by an expanding ring. A substantially rigid ring is connected by a pivot to each of the linkage arms at a point between the arm's outer end and its inner pivot connection to the optic. The substantially rigid ring has a diameter smaller than the minimum equatorial diameter of the capsule, but larger than the optic and generally coaxial to it. The pivots on the rigid ring serve as fulcrums, and the linkage arms act as levers, rotating about the fulcrums when the capsule's equatorial diameter changes. In accordance with Schachar's theory, the linkage arms may be constructed so that when the equatorial diameter of the capsule increases, said lever action will cause the optic to move forward.

An alternative embodiment of the invention, in accordance with Helmholtz's theory, similarly includes rigid or resilient linkage arms, connected to a rigid ring with pivots acting as fulcrums for lever action of the arms, as in the preceding embodiment. In this alternative embodiment, however, the linkage arms are constructed so that when the equatorial diameter of the capsule decreases, said lever action will cause the optic to move forward.

In a further preferred embodiment of the invention, two optics are used, one of which is adjacent to the posterior wall of the lens capsule and the other is held parallel and anterior to it, with an intervening space between them. The refractive power of the optics and the spacing between them is so designed that when the ciliary muscle is relaxed, distant objects are focused onto the retina. Each optic is held in place by two or more linkage arms or haptics, which are shaped and positioned in such a way as to cause each of the arms of the anterior optic to come into contact with and cross a corresponding arm of the posterior optic, at a pivot point along or near the equatorial plane of the capsule.

These points of contact of the corresponding anterior and posterior linkage arms are located at a radius from the center of the capsule that is greater than the radii of the two optics but smaller than the total equatorial radius. The outer ends of the arms are flexibly anchored to an expanding ring at the edge of the lens capsule, adjacent to the zonules. When the ciliary muscle contracts and the equatorial diameter of the capsule decreases, in accordance with Helmholtz's theory, the angle of crossing between the corresponding anterior and posterior linkage arms increases in a scissors-like action, which in turn increases the spacing distance between the anterior and posterior optics. As this spacing increases, the laws of optics provide that the refractive power of the lens couple will decrease, thereby allowing near objects to be focused onto the retina. The illustrated embodiment operates according to the Helmholtz theory. Similar embodiments, utilizing the same principles can be applied to design of lens couples which operate according to the Schachar theory.

One aspect of the present invention also provides means and method for the surgeon to adjust the focusing mechanism during or after implantation, so as to optimize the near and distant focus of the intraocular lens assembly. While the large range of optic motion afforded by the invention may allow the patient to achieve full near and distant accommodation without the need for adjustment, surgical adjustment of the focal position may improve post-operative vision in cases where this full motion cannot be achieved.

For this purpose, alternative preferred embodiments of the invention provide for either a rigid ring, coaxial with and surrounding the optic, or the linkage arms, or both of these structures, to be formed with a plurality of kinks. A tool is provided for the purpose of straightening the kinks in the ring in a controlled and graduated manner, so as to increase the diameter of the ring, causing the optic to move away from the capsule wall and closer to the equatorial plane of the capsule. A further tool is provided for straightening the kinks in the linkage arms, thereby moving the pivot fulcrum points of the linkage arms away from the optic and pushing the optic farther back in the capsule. The surgeon may thus adjust the position of the optic when the ciliary muscle is relaxed, so as to achieve the best focus of distant objects on the retina. When the ciliary muscle contracts, the entire range of motion of the edge of the capsule adjacent to the zonules will be utilized to achieve accommodative motion of the optic within the capsule.

There is therefore provided, in accordance with a preferred embodiment of the invention an intraocular lens assembly for implantation in a human eye, said eye including a ciliary muscle and zonules controlled by the ciliary muscle, the assembly comprising:

an optic having anterior and posterior surfaces depending from a common edge;

at least two linkage arms, each being attached to the optic at a first position on the arm thereof and cooperating with ciliary muscle or the zonules at a second position on the arm; and at least two pivots, one of which is rotatably attached to each respective linkage arm intermediate the first and second positions.

There is further provided, in accordance with a preferred embodiment of the invention, an intraocular lens assembly for implantation in a human eye, said eye including a ciliary muscle and zonules controlled by the ciliary muscle, the assembly comprising:

an optic having anterior and posterior surfaces depending from a common edge; and at least two substantially rigid linkage arms, each being attached to the optic at a first position on the arm thereof and cooperating with ciliary muscle or the zonules at a second position on the arm.

There is further provided, in accordance with a preferred embodiment of the invention, for use with the intraocular lens assembly according to the above preferred embodiments in which kinks are provided in said linkage arms or in an optional rigid ring, an adjustment tool for removing said kinks, the adjustment tool comprising:

a pincer having a pair of handles and two pairs of aligned jaws opposite said handles rotatable about a hinge axis, for insertion into the ciliary body and supporting thereon respective ones of said kinks, such that closing the handle presses the kinks between respective pairs of said jaws thereby flattening the kinks.

There is further provided, in accordance with a preferred embodiment of the invention, for use with the intraocular lens assembly according to the above preferred embodiments in which kinks are provided in said linkage arms or in an optional rigid ring, an adjustment tool for removing said kinks, the adjustment tool comprising:

a pincer having a pair of handles and a pair of substantially planar support members opposite said handles rotatable about a hinge axis, for insertion into the ciliary body and supporting thereon respective ones of said kinks, and a pair of flattening members cooperating with the support members for pressing the kinks towards the support members and thereby flattening the kinks.

There is further provided, in accordance with a preferred embodiment of the invention, an intraocular lens assembly for implantation in a human eye, said eye including a ciliary muscle and zonules controlled by the ciliary muscle and at least a portion of a lens capsule including an edge thereof and at least a portion of a posterior wall thereof, the assembly comprising:

an expanding ring associated with the edge which contacts the edge portion of the lens capsule and preferably the posterior wall and positions the posterior wall toward the back of the eye from center of the lens capsule; and an optic associated with the expanding ring.

There is further provided, in accordance with a preferred embodiment of the invention, an intraocular lens assembly for implantation in a human eye, said eye including a ciliary muscle and zonules controlled by the ciliary muscle and at least a portion of a lens capsule including an edge thereof, the assembly comprising:

an expanding ring associated with the edge portion of the lens capsule and which provides a resilient radial force on the edge; and an optic associated with the expanding ring.

Preferably, the expanding ring bears against the edge of the lens capsule and provides an outward radial force or is attached to the edge and provides an inward radial force.

There is further provided, in accordance with a preferred embodiment of the invention, an intraocular lens assembly for implantation in a human eye, said eye including a ciliary muscle and zonules controlled by the ciliary muscle and at least a portion of a lens capsule including an edge thereof and at least a portion of a posterior wall thereof, the assembly comprising:

an expanding ring associated with the edge comprising alternating rigid and elastic portions; and an optic associated with the expanding ring.

BRIEF DESCRIPTION OF THE DRAWINGS

In order to better understand the invention and to see how it may be carried out in practice, some preferred embodiments will now be described, by way of non-limiting example only, with reference to the accompanying drawings, in which:

FIGS. 2A and 2B are front and side views of a preferred embodiment of the optic shown in FIG. 1;

FIG. 3 is a front cross-sectional view of a preferred embodiment of the expanding ring shown in FIG. 1;

DETAILED DESCRIPTION OF PREFERRED EMBODIMENTS

Figure 1:
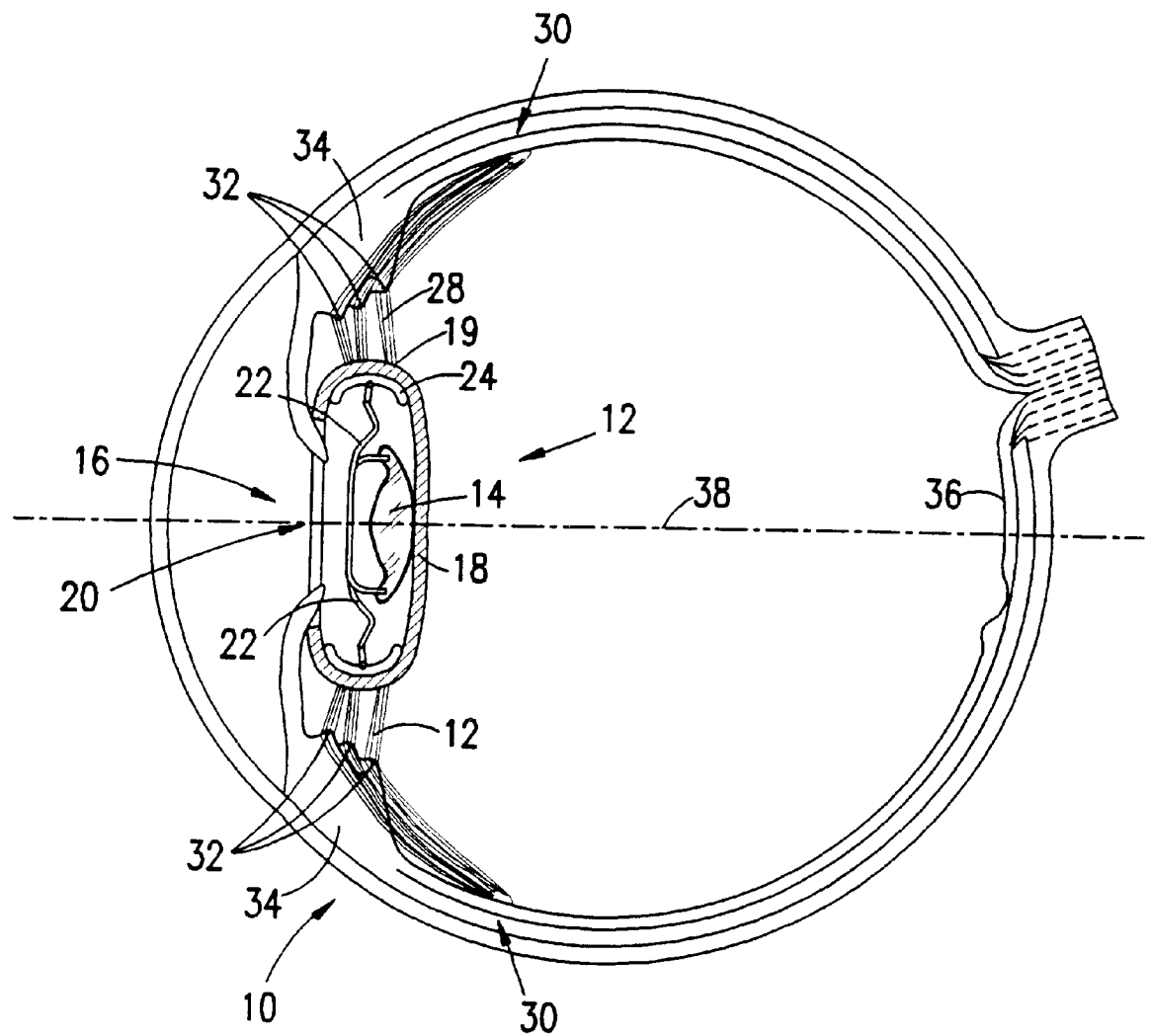
FIG. 1 shows a cross-sectional view of an eye having therein a lens capsule containing an intraocular lens assembly according to a preferred embodiment of the invention.

FIG. 1 shows a cross-section of a human eye 10 having an adaptive intra-ocular lens system 12, in accordance with a preferred embodiment of the invention, installed in place of the original material in a lens capsule 16. In this and all other cross-sectional diagrams of the eye and structures therein, the cornea and other anterior portions of the eye are at the left of the figure, and the retina and posterior portions of the eye are to the right. Intraocular lens system 12 comprises an optic 14 placed within lens capsule 16. Lens capsule 16, from which the original lens material has been removed, includes an outer edge 19, which is left intact and, optionally, a posterior wall 18 at least a portion of which may be left intact. At least a portion of the original anterior wall of the capsule is generally removed during the operation for removal of the lens material leaving an opening 20, through which the lens system is installed.

As shown more clearly in FIGS. 2A, 2B, and 3, lens system 20 also includes two or more linkage arms 22, also known as haptics, which are attached to the optic 14 at one end of the arms and which preferably rest on or are pivotably attached to an expanding ring 24 at a second end thereof. In a preferred embodiment of the invention shown in FIGS. 1–3, arms 22 are pivotably attached for limited rotational motion at pivots 26, symmetrically placed on the outer edge of the optic 14, and at pivots 27 on expanding ring 24.

As shown in FIG. 1, one end of zonular fibers 28, also known as zonules, is attached to edge 19 of lens capsule 16. The other end of the zonules is attached to the sclera 30 of the eye. Intermediate their ends, the zonular fibers are acted upon by ligaments or the like 32 which are controlled by ciliary muscle 34. The portion of the eye comprising the ciliary muscle and the volume it encloses is also known as the ciliary body.

Optic 14 produces an image on the retina at the back of the eye 10 corresponding to a focal plane 36. In order to provide accommodation, optic 14 is made capable of movement along optical axis 38. As in the normal eye, accommodation is made consequent to changes in tension of the zonular fibers. This change in tension acts on optic 14 so as to alter the image distance from optic 14 to focal plane 36.

In the preferred embodiment shown in FIGS. 2A and 2B, linkage arms 22 are made of a relatively rigid material and are attached to the outer edge of optic 14 at pivot 26. The pivot may be made of flexible material, which allows twisting or rotation of the arms about the pivot in response to rotational force applied to the arms 22, but prevents substantial axial motion of the arms. This flexible material may also be elastic, so that pivots 26 will exert a biasing force on arms 22, which will tend to return optic 14 to its original position when the rotational force applied to the arms is removed. Alternatively, pivot 26 may be made of rigid material with a bore through which arm 22 is inserted and fastened in such a way that the arm may rotate about the axis of the bore, but any substantial axial motion along the axis of the bore is prevented.

Figure 4A:
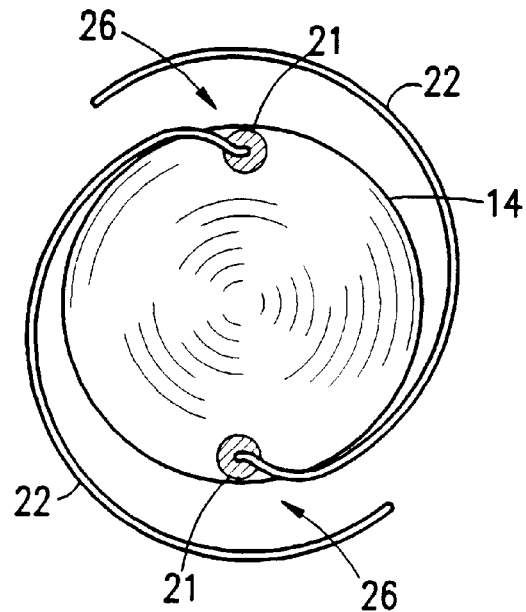
FIG. 4A and 4B are front and side, partially sectioned, views of an alternative preferred embodiment of the optic shown in FIG. 1.
Figure 4B:
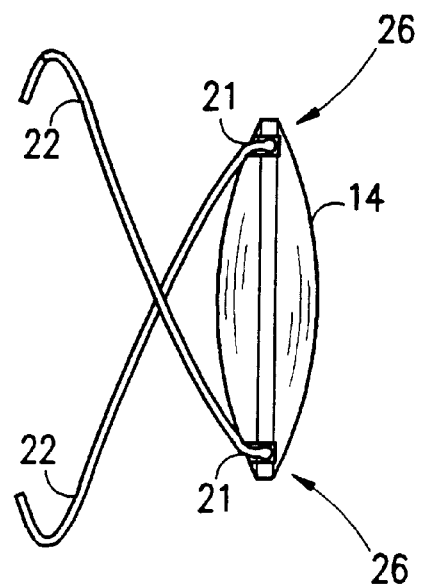

Other constructions for the linkage arms 22 and for their attachment to the optic may also be provided. In an alternative preferred embodiment shown in FIGS. 4a and 4b, rigid linkage arms 22 are pivotably attached to the face of optic 14. Pivots 26 may in this case be constructed in the form of an indentation 21 in the face of optic 14, which is filled with a flexible plastic material, and in which the end of linkage arm 22 is embedded. In this manner, the angle between linkage arm 22 and the optical axis 38 of optic 14 may change in response to radial forces exerted on the linkage arm, due to flexing of pivot 26. Alternatively or additionally, portions of the haptics which are adjacent to 26 are also made flexible.

Within the context of the invention the terms "rigid" and "flexible" or "resilient" have a special meaning. The haptics attached to the optic in prior art, such as in the Woods patent, to which reference has been made, are, in fact, resilient wires formed of plastics or any other biologically inert material. They are sufficiently stiff so that when a compressive force is applied thereto, they distort but do not buckle. Rather, they push the optic to which they are attached forward along the optical axis. However, they are also sufficiently resilient so that when the compressive force is reduced, they spring back under their own elasticity so as to return the optic toward its original position. It is this property, namely that a compressive force applied to the lever arms does not cause them to buckle or otherwise collapse, which is essential for prior art inventions, and it is to this extent that the term "flexible, resilient" is to be understood herein.

Many preferred embodiments of the present invention, however, use substantially rigid elements, and in particular substantially rigid linkage arms or haptics. These elements are considered to be rigid because, in these embodiments, they do not deform significantly under the compressive or tensile forces present during accommodation. They are, therefore, capable of transmitting forces applied to them more efficiently than flexible elements and potentially with greater mechanical advantage. It is in this context that the term "rigid" is to be understood in relation to the present invention. It should be understood, however, that these "rigid" segments are made of very thin material and may not be rigid under other circumstances, such as during surgical implantation, when greater force is applied to them so that they can be inserted into the lens capsule.

Expanding ring 24 is constructed so as to exert an outward radial force, which will cause the ring to conform to the edge 19 of lens capsule 16, and expand or contract in response to expansion or contraction of the capsule, respectively. Ring 24 serves to couple the outer end of linkage arms 22 to edge 19, so that radial forces exerted by zonules 28 and ciliary muscle 34 can act upon said arms. Ring 24 may further serve to open capsule 16, i.e., to separate the anterior and posterior portions of the lens capsule, in place of the natural lens that was surgically removed, so that the elasticity of the capsule may serve more advantageously to exert inward radial force on the lens assembly as described below.

In a preferred embodiment, shown in FIG. 3, ring 24 comprises alternating segments of rigid and compressible materials. Rigid segments 25 ensure that ring 24 maintains its circular shape and that the capsule does not collapse.

Compressible segments 29 exert tangential force on adjacent rigid segments, causing the ring to expand if it is not radially constrained. In the embodiment described here, radial constraint is provided by edge 19 of the lens capsule which is constrained from outward movement by the resilient nature of the lens capsule.

In the preferred embodiment shown in FIG. 3, the ring includes pivots 27, to which the outer ends of linkage arms 22 are attached. Such attachment may be made at the time of manufacture of assembly 12, and pivots 27 may be similar in construction to pivots 26 on the optic, as described above. In an alternative embodiment, expanding ring 24 is manufactured separately from optic 14 and linkage arms 22. Expanding ring 24 may then be implanted in capsule 16 by the surgeon. The surgeon may next position the optic and insert the linkage arms into receptacles on the expanding ring, such receptacles being produced in such a way as to permit the ends of the linkage arms to be pressed or snapped into them and held thereby, so that the linkage arms may pivot about their axes while remaining permanently fixed therein. Such a receptacle is shown for example in FIG. 10.

In another alternative embodiment thereof, expanding ring 24 may be provided without pivots. The outer ends of linkage arms 22 bear against the inner surface of expanding ring 24, but are not fastened thereto, and are thus free to rotate about their own axes.

In a further alternative embodiment, expanding ring 24 may be eliminated, and linkage arms 22 may instead be rotatably coupled at their outer ends to anchors, which may be glued or sutured to capsule edge 19, zonules 28 or less preferably, ciliary muscle 34. More preferably, the expanding ring is not eliminated but is provided as a split ring so that it exerts no force of its own in the radial direction while preserving the lens capsule in an open condition.

The preferred embodiments of the invention shown in FIGS. 1–4 and in FIGS. 6 through 12 will generally be described herein in terms of rigid linkage arms 22, pivotably attached to expanding ring 24 and/or to a relatively rigid ring. It will be appreciated, however, that some embodiments of the invention may incorporate either rigid or flexible, resilient linkage arms 22. Furthermore, the linkage arms may generally be coupled to optic 14 and to edge 19 of the capsule or zonules 28 according to any of the embodiments described herein.

Figure 5:
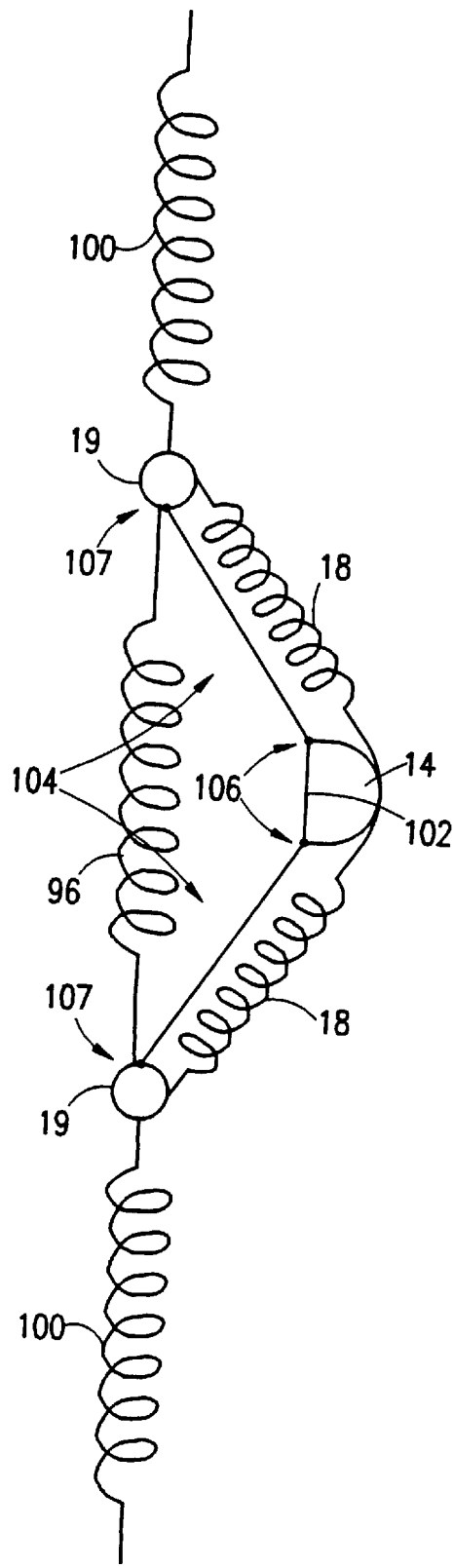
FIG. 5 is a schematic representation of the intraocular lens assembly according some aspects of the present invention, useful for explaining the mechanical operation thereof.

FIG. 5 shows a schematic representation of the intraocular lens assembly according some aspects of the present invention, useful for explaining the mechanical operation thereof and in particular in illustrating the action of the forces that operate on intraocular lens system 12, during accommodative motion of optic 14. The embodiment of the present invention that is shown in FIGS. 1–4 may be considered to be one preferred embodiment of the more general scheme shown here in FIG. 5.

While FIG. 5 generally follows Schachar's theory of accommodation, it should be understood that the principles of the present inventions are equally applicable to the Helmholtz theory of accommodation, as will be shown in some of the examples described below.

In FIG. 5, the posterior wall 18 of the lens capsule contacts the rear surface of optic 14. The resilience of the posterior wall is indicated by springs to indicate that the resilient wall biases the optic to the left, i.e., to the front of the eye. An optional tensive element 96 may be further provided between the ends 19 of the lens capsule as described above. Additionally, the edge of the lens capsule also acts as a tensive element 96. In addition the expanding ring, not shown in FIG. 5, for simplicity, may be present and may partially counteract the effect of the posterior wall and tensive element 96.

One way of providing tensile elements 96 is to attach an elastic ring, which is preferably in tension during both far and near vision, to the zonules or to the edge of the lens capsule. This attachment may be by suturing the elastic ring to the edge of the lens capsule. Preferably, when such tensive action is required, as for example, when the posterior wall is removed, the expander ring is made tensive, in use, rather than being in compression as described above. Such a ring would be implanted by expanding the ring utilizing a removable expanding ring, suturing the ring to the edge of the lens capsule and then removing the expansion ring. This type of tensile member effectively reinforces the inherent tension of the edge of the lens capsule itself.

The edge of the lens capsule is connected to springs 100 which represent the effect of the zonules.

At least two linkage arms 104 are connected to opposing the edges of optic 14 where they are rotatable about pivots 106. The corresponding outer positions on arms 104 bear against the ends 19 of the lens capsule. where they pivot at pivot points 107. As described above, in preferred embodiments of the invention an expanding ring 24 may intervene between arms 104 and zonules 100, although arms 104 may also be secured to the zonules by gluing or suturing. For the sake of simplicity, these elements are not shown in FIG. 5. Furthermore, although arms 104 are shown having substantially the form of the embodiment of FIGS. 1–4, they may have the forms shown below in the other embodiments of the invention, as appropriate.

The outward radial tension which is applied to lens capsule edge 19 by zonules 100, which tension may be considered to include, as well, outward radial force exerted by expanding ring 24 in some preferred embodiments of the invention.

In general, the axial position of the optic depends on the balance of forces between the zonules 100 (and the expanding ring, if present) which urge edge 19 of the lens capsule outward and the resilience of the lens capsule (and tensile element 96, if present) which urges the edge of the lens capsule inward. The effect of the force of the posterior wall 18 of the lens capsule on the optic also tends to push edge 19 of the lens capsule, outward. In many embodiments of the invention the urging of the optic by the posterior wall enables the expanding ring 24 and the outer end position on the linkage arms to be held in place without any attachment of the lens assembly to the lens capsule or to the zonules. This simplifies implantation considerably.

In the arrangement shown in FIG. 5, increased outward radial force on zonules 100, generally due to contraction of the ciliary muscle, induces outward motion of edge 19. This motion results in a net radial movement of the outer ends of linkage arms 104, whereby tension in the posterior wall (and tensile element 96, if present) is increased. This will cause lens 14 to move forward (to the left), until a new balance of forces is reached.

When the radial force on zonules 100 is reduced, edge 19 moves back inward, which would cause a reduction of the tension in the posterior wall in the absence of optic 14. However, this reduction in tension is at lease partially mitigated by pressure from the optic which is forced against the posterior wall by the inward movement of the outer edge of arms 104.

It may be appreciated that in preferred embodiments of the present invention, a wide variety of mechanical designs may be applied to the intraocular lens system and, more specifically, to linkage arms 104 and pivots 106 and 107, with the objective of increasing and otherwise controlling the axial displacement of optic 14 resulting from radial forces applied at pivots 107. Preferably, the ratio of axial to radial displacement is large enough to provide at least 5:1 amplification of the radial motion, so as to provide substantially complete accommodation. In saying this, it is understood that complete accommodation requires an axial movement of the optic 14 of approximately 1 mm whilst the maximum radial movement of the ciliary muscle 34 is approximately 200 micrometers. However, it will be appreciated that other ratios may be employed as required. In particular, a larger ratio will result in a range of accommodation which is larger than required for near/far vision. When such larger accommodation ratios are available, the exact placement of the optic becomes less critical since the contraction of the ciliary muscle will be sufficient to provide full accommodation even if far vision is overcompensated when the ciliary muscle is relaxed.

Figure 6B:
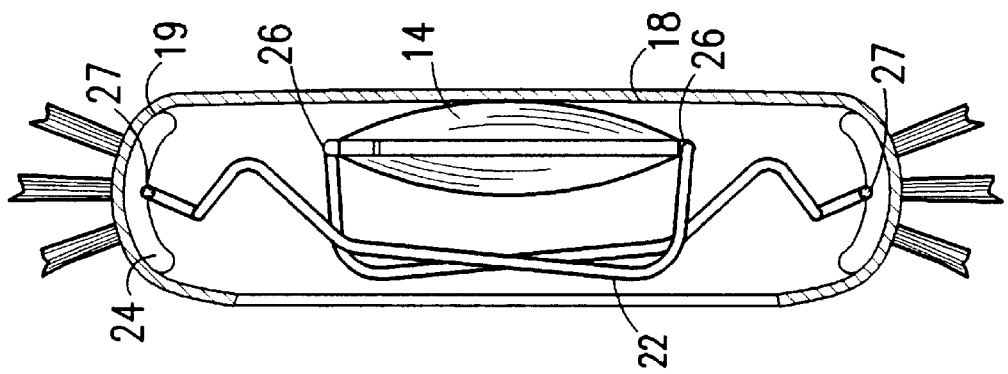
FIGS. 6A and 6B are respective sectional elevations of a preferred embodiment of the invention, which operates in accordance with Schachar's theory of accommodation, showing the relative displacement of the optic for far vision and near vision, respectively.
Figure 6A:
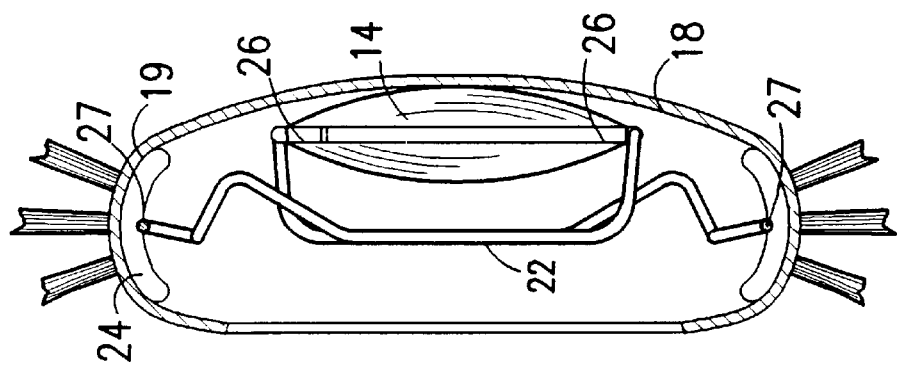

FIGS. 6A and 6B are partial cross-sections showing a detail of a preferred embodiment of the intraocular lens assembly 12 depicted in FIG. 1 and showing more clearly the construction and operation of the linkage arm 22 and pivots 26 and 27. Linkage arms 22 are characterized by a radial reach and axial reach. Radial reach is defined herein as the sum of the respective radial distances of pivots 26 and 27 from the optical axis. Axial reach is defined as the difference between the relative axial positions of these pivots. Because the radial reach of linkage arm 22 is greater than the axial reach, a small radial movement applied to the outer end of arm 22 gives rise to a correspondingly greater axial movement of the inner end to which the optic 14 is attached.

In operation, in response to changes in the tension of the zonular fibers 28, edge 19 of lens capsule 16, which is adjacent to the fibers, moves radially in and out. This radial movement causes force to be exerted on arms 22, thereby causing the arms to rotate about pivots 26 and 27. It will be appreciated that outward motion of the edge 19 of the lens capsule 16 will cause the outer end of arm 22, which is attached to the expanding ring 24, to move radially away from the optical axis 38, and the inner end of arm 22 will then-move axially forward, away from the focal plane 36 of the eye.

In FIG. 6A, the zonular fibers 28 are at their maximal extension, corresponding, in accordance with Schachar's hypothesis, to accommodation of the eye for distant vision. In this case optic 14 presses against the posterior wall 18 of the capsule, at such distance from focal plane 36 as to create a focused image at the focal plane of objects distant from the eye. In FIG. 6B, where accommodation of the eye for near vision is shown, zonular fibers 28 have contracted, pulling edge 19 of the capsule outwards, and causing linkage arms 22 to rotate about pivots 26 and 27, so that optic 14 moves to the left, away from the retina, to such distance from the focal plane 36 as to create a focused image at the focal plane of objects near the eye. In the configuration shown in FIGS. 6A and 6B, pressure of posterior wall 18 of capsule 16 may exert a forward resilient biasing force on optic 14 which moves the optic to the left when the tension in the zonules increases, as described above.

When the eye returns to distant vision accommodation, zonular fibers 28 extend, causing outer edge 19 of the capsule to contract due to inward radial force exerted by the elastic capsule. As a result of this contraction, linkage arms 22 will rotate back to the position shown in FIG. 6A and will return optic 14 to its distant focus position.

As noted above, in the preferred embodiment of the invention described with reference to FIGS. 6A and 6B, an expanding ring 24 with pivots 27 is used to couple linkage arms 22 to the edge of the capsule 19 and zonules 28, and to exert an outward radial biasing force. Pivots 26 are provided to connect arms 22 to the edges of optic 14. Further as described above with respect to FIG. 5, capsule wall 18 exerts an inward radial force on the edge 19 of the capsule and a forward biasing force on the optic. We note, however, that the mechanical principles operative in the embodiment shown in FIGS. 6A and 6B could more generally be applied to alternative preferred embodiments of the invention, utilizing other types of linkage arms, pivots and couplings, as are described hereinabove. These alternative elements could similarly be used in the preferred embodiments of the invention to be described below.

Figure 7B:
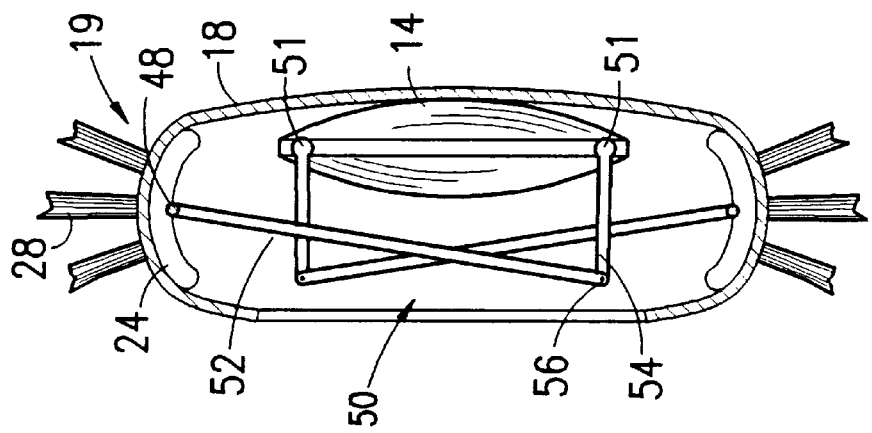
FIGS. 7A and 7B are respective sectional elevations of a preferred embodiment of the invention, which operates in accordance with Helmholtz's theory of accommodation, showing the relative displacement of the optic for far vision and near vision, respectively.
Figure 7A:
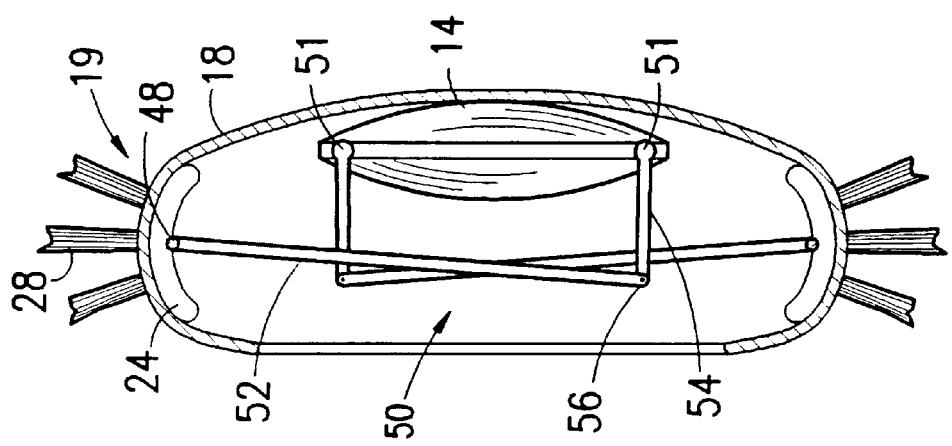

FIGS. 7A and 7B show another preferred embodiment of the invention that operates under the Helmholtz theory of accommodation. In this case, it will be appreciated that when the eye accommodates for near vision, zonular fibers 28 relax, causing edge 19 of the capsule to move inward. In this embodiment, optic 14 is connected to expanding ring 24 by a pair of articulated linkages 50. Each linkage comprises an outer arm 52 and an inner arm 54, connected together by a pivot joint 56. Outer arm 52 is attached to the expanding ring 24 by a pivot 48, which permits the linkage to rotate in the plane of the cross section. Inner arm 54 is fixed rigidly to optic 14 at point 51.

When the eye accommodates for distant vision, optic 14 rests against posterior wall 18 of the capsule at a distance at which a focused image of distant objects is formed on the retina. When the eye accommodates for near vision, edge 19 of the capsule moves inward, causing pivot 48 to move radially inward and outer arm 52 to rotate clockwise about pivot 48. Pivot 56 moves forward, to the left as shown in FIG. 7B, causing optic 14 to be drawn forward to a position farther from the retina, thus allowing focused images of objects near the eye to be formed on the retina. In this embodiment of the invention, outer arm 52 must be pivotably attached to ring 24 which is also preferably attached to or biased against edge 19 of the lens capsule. In this way the motion of edge 19 is reliably transmitted to outer arm 52.

Figure 8B:
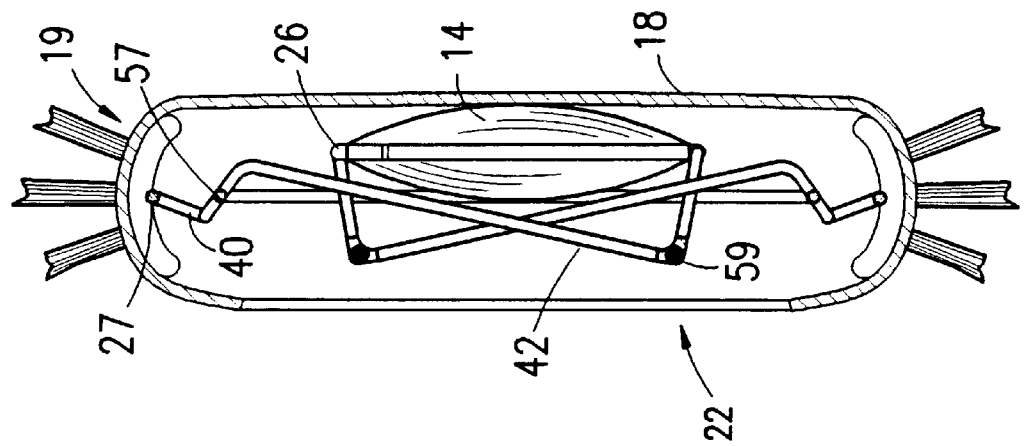
FIGS. 8A and 8B are respective sectional elevations of an alternative preferred embodiment of the invention, which operates in accordance with Schachar's theory of accommodation, showing the relative displacement of the optic for far vision and near vision, respectively.
Figure 8A:
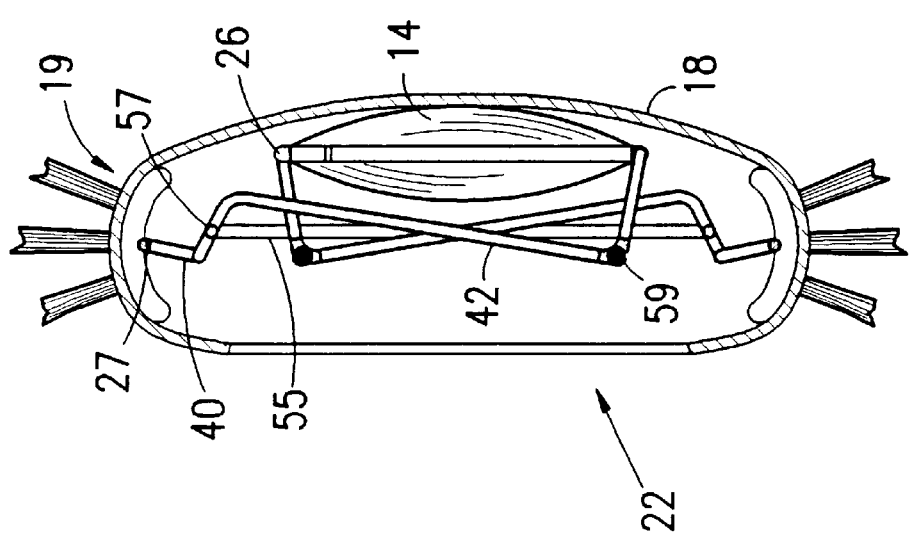

In another preferred embodiment of the invention, shown in FIGS. 8A and 8B, and described herein in reference to Schachar's theory of accommodation, the linkage arms may be configured as levers, so as to further amplify the radial motion of capsule edge 19. A rigid ring 55, whose diameter is larger than that of the useful area of the optic but smaller than the minimum equatorial diameter of the lens capsule, is connected to the linkage arms by pivots 57, and which are positioned to hold ring 55 coaxial with optic 14.

Figure 9:
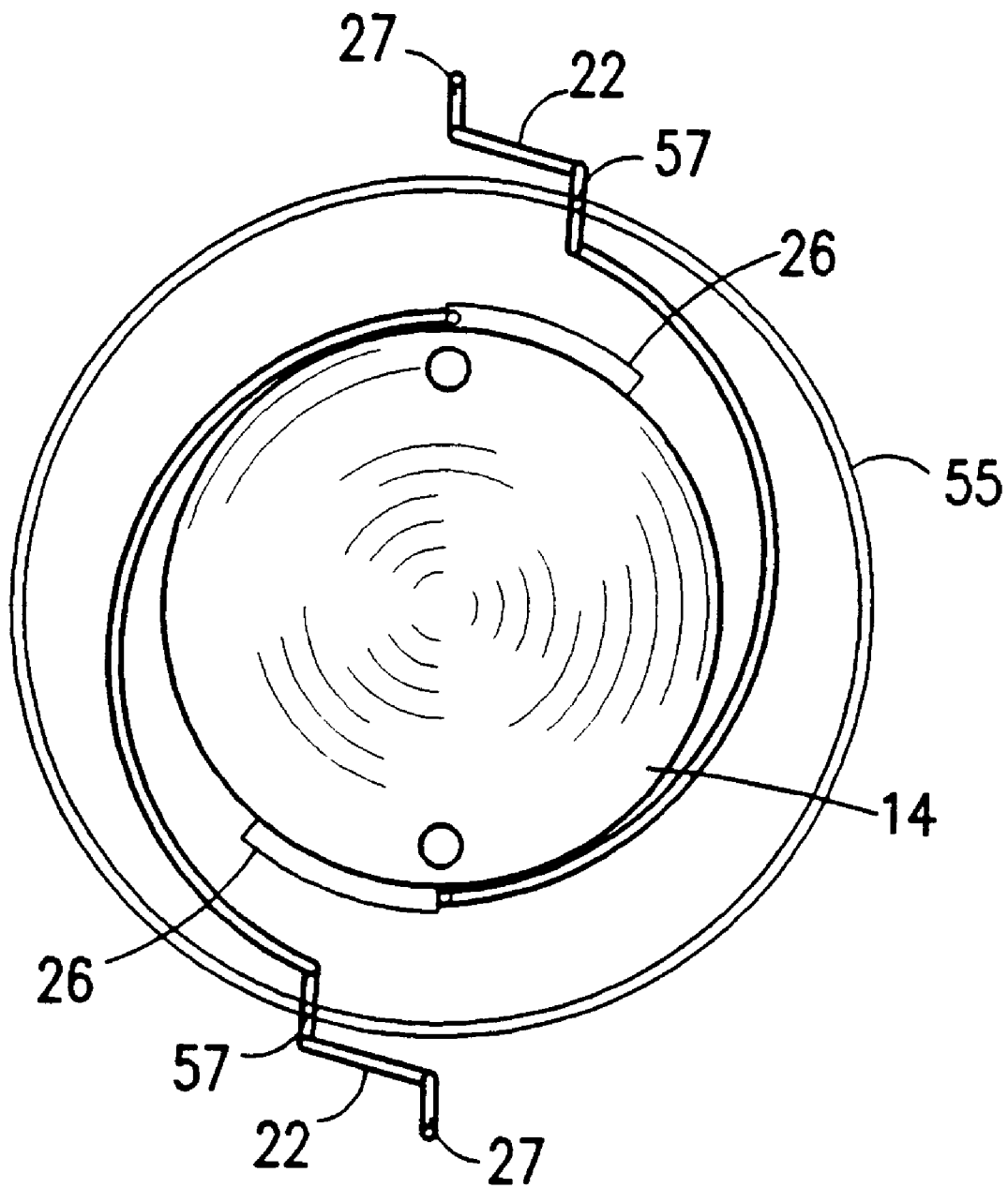
FIG. 9 is a front view of a preferred embodiment of the optic shown in FIGS. 8A and 8B.
Figure 10:
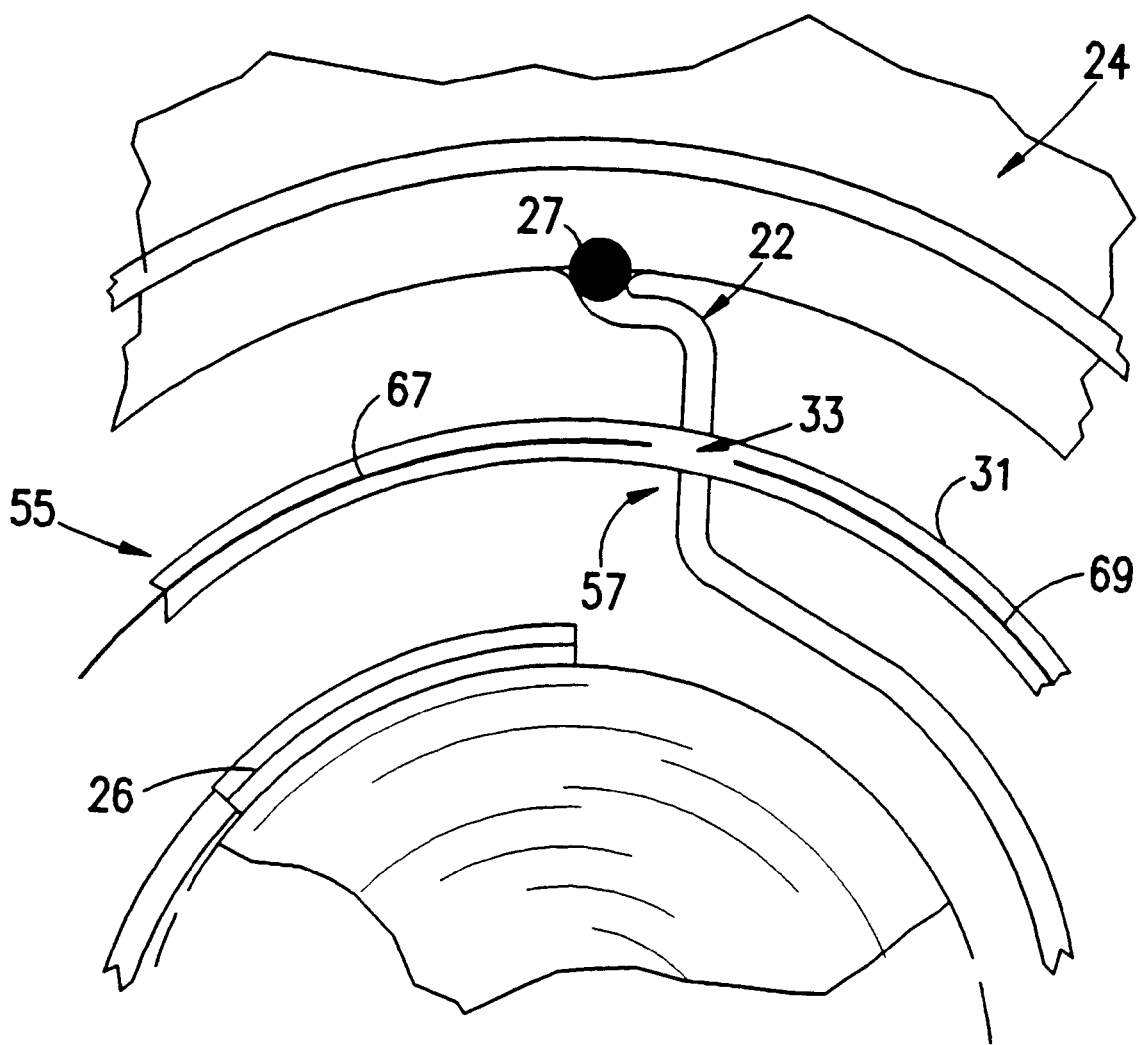
FIG. 10 is an enlarged view of a preferred embodiment of a pivot mechanism used in the embodiment of FIG. 9.

Ring 55 is shown in front view in FIG. 9, together with optic 14 and linkage arms 22. FIG. 10 shows a detail of the construction of a preferred embodiment of linkage arm 22, ring 55 and pivot 57 shown in FIG. 9. Ring 55 has at least two sections 67 and 69, which are interconnected by a biologically inert elastic sleeve 31 which fits over the junction of the two sections 67 and 69 so as to leave a small gap 33 therebetween which, owing to the elasticity of the inert sleeve, allows twisting of the adjacent sections 67 and 69 of the pivot 57. The portion of the inert sleeve 33 intermediate the two sections 67 and 69 of the ring 22 is anchored to the linkage arm 22 so that, consequent to application of radially directed force to the outer section of the arm 22, the sleeve 33 twists, thereby allowing rotation of the arm about pivot 57. By means of this construction, the natural tendency of the biological tissue to grow around the inert sleeve 33 owing to attempted rejection by the body of the intraocular implant, which constitutes foreign matter, does not impede the performance of pivot 57.

The pivot embodiment described here in reference to pivot 57 on ring 55, based on a flexible sleeve or other flexible element coupling two rigid elements, may also be useful in other pivots used in other preferred embodiments of the invention, such as pivot 56, shown in FIGS. 7A and 7B, and pivot 59 in FIGS. 8A and 8B.

Referring again to FIGS. 8A and 8B, it may be seen that when zonules 28 draw the edge 19 of the capsule radially outwards, as the eye accommodates for near vision, arms 22 will act as levers, rotating about pivots 57, which serve as fulcrums. Linkage arms 22 further pivot at pivot connections 26 and 27, to the optic 14 and expanding ring 24 respectively, and flex at joint 59. Thus, the inner portions 42 of the linkage arms 22, will pull the optic 14 axially forward. The mechanical advantage of the levers, due to the inner lever arm 42 being substantially longer than outer lever arm 40, will amplify small radial movements of the edge of the lens capsule 28 into larger axial movements of optic 14.

Figure 11A:
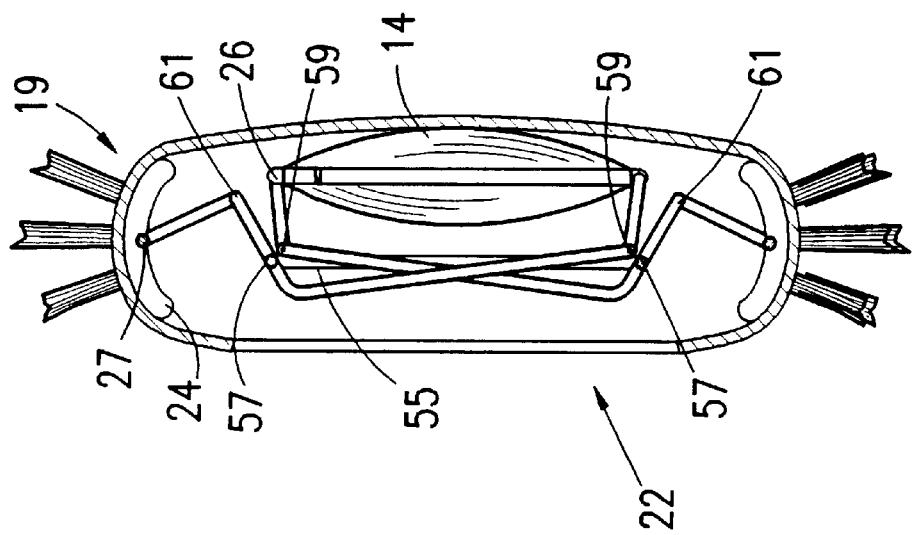
FIGS. 11A and 11B are respective sectional elevations of a preferred embodiment of the invention, which operates in accordance with Helmholtz's theory of accommodation, showing the relative displacement of the optic for far vision and near vision, respectively.
Figure 11B:
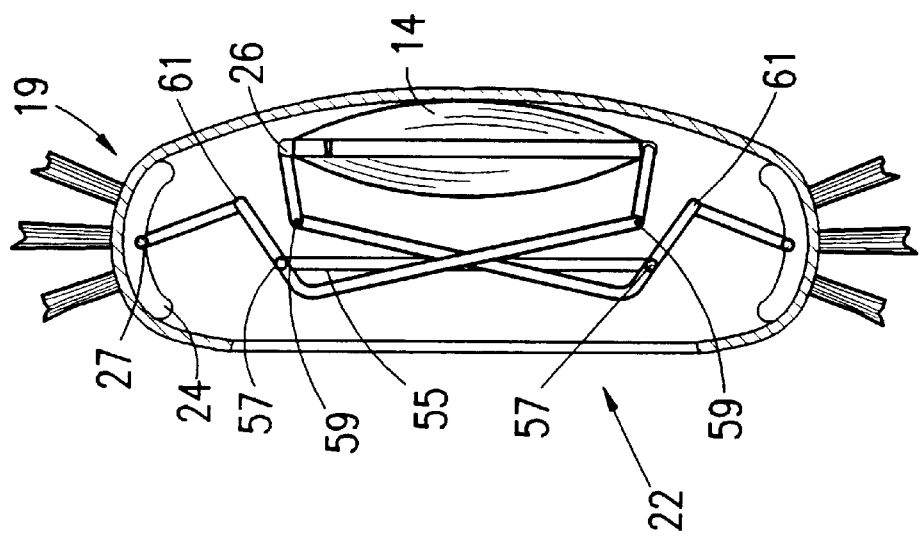

FIGS. 11A and 11B show a cross-sectional view of another preferred embodiment of the invention, operable under the Helmholtz theory of accommodation. This embodiment is similar to the preceding one, using linkage arms 22 as levers, with pivots 57 on rigid ring 55 serving as fulcrums. In the present embodiment, however, linkage arms 22 are so configured that when accommodation of the eye for near vision causes the edge 19 of the capsule to move radially inward, linkage arm 22 will rotate about pivot 57 in such a way as to cause optic 14 to move axially to the left, away from the retina, as required for near accommodation. Preferably, at least portions 59 and, optionally, 61 of arm 22 are flexible to allow the arm to rotate about pivot 57. Furthermore, pivot 26 is provided between the arm and the optic as described above.

It may be appreciated that other preferred embodiments of the present invention may use linkage arms 22 that are formed of flexible, resilient material, as discussed earlier, with or without expanding ring 24. Rigid ring 55 is still provided, with pivots 57 to act as fulcrums for the lever action of arms 22. In these embodiments, the resilient arms 22 are mechanically pre-loaded and hold the optic 14 in place by pressure of their outer ends against the edges 19 of the capsule. Such embodiments still utilize the same mechanical leverage principles as the preceding embodiments, which are based on rigid linkage arms.

Figure 12:
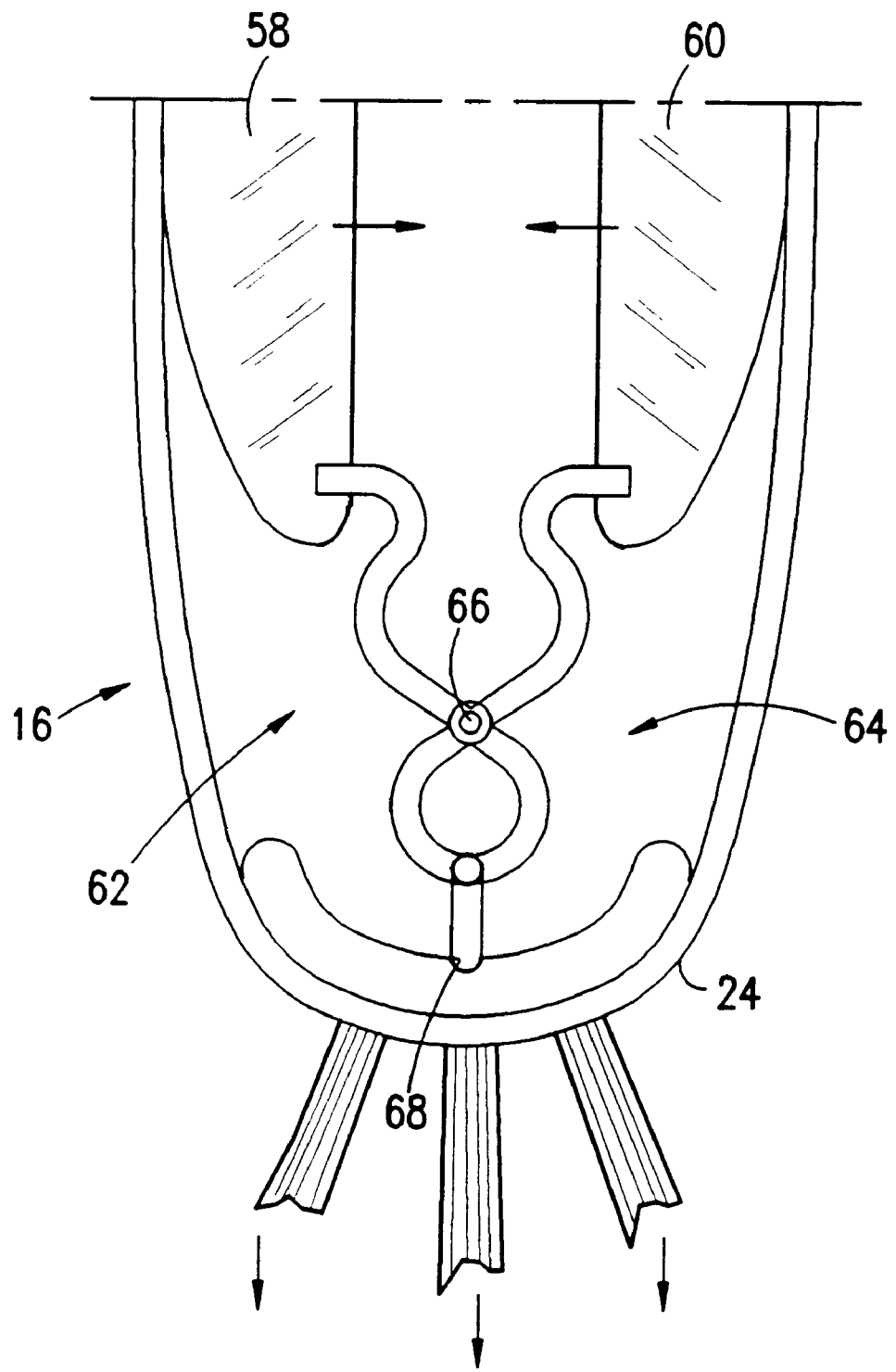
FIG. 12 is a half-sectional elevation of a modified intraocular lens assembly comprising two optics.

FIG. 12 shows, in cross-section, another embodiment of the invention wherein a lens doublet comprising a pair of optics 58 and 60 are employed, commonly connected by respective linkage arms 62 and 64, commonly hinged to a pivot 66 and anchored to a peripheral expanding ring 24 within the lens capsule 16. The various embodiments described earlier with reference to the flexibility or rigidity of the linkage arms, the methods of mounting them to the optics and the methods of coupling them to the motion of the zonules, also apply to the lens doublet shown in FIG. 12. Optics 58 and 60 and the distance between them are chosen so that when the zonules are relaxed, the refractive power of the lens doublet is such as will cause focused images of distant objects to be formed on the retina.

In the arrangement shown in FIG. 12, following Helmholtz's theory of accommodation, contraction of the ciliary muscle results in an inwardly directed radial force being applied to lever arms 62 and 64, resulting in mutual counter-rotation thereof whereby optics 58 and 60 are pushed farther away from each other. As explained by Sarfarazi in U.S. Pat. No. 5,275,623, is incorporated herein by reference, increasing the distance between optics 58 and 60 will decrease the refractive power of the lens doublet, thereby causing objects nearer the eye to form focused images on the retina, so that when the ciliary muscle contracts, the eye is accommodated for near vision.

The actual focal length of optic 14 which is to be implanted within the lens capsule 16 is a function of the size of the eyeball and refraction (myopia or hyperopia) of the eye, among other things, and will vary from patient to patient. An advantage of the present invention is that the mechanism it provides for accommodative movement of optic 14 within capsule 16 causes the small radial motion of the edge 19 of capsule wall to be amplified into a relatively larger axial motion of the optic. This large accommodative movement enables the eye to achieve a full range of accommodation, from distant to near vision, and can compensate for differences in the sizes of the eyeball and refraction from patient to patient.

For some patients, however, it may be desirable to provide for position adjustment within lens capsule 16, so that optic 14 will be located at a suitable distance from the center of the lens capsule, such that when the ciliary muscle is completely relaxed, the eye is correctly focused on infinity, this being the correct adjustment for far vision. In practice, it is very difficult to position the optic precisely during the implantation surgically without a certain amount of trial and error, and therefore means are preferably provided for allowing small adjustments to be made to the axial displacement of optic 14. However, it is possible to measure the refraction of the lens in situ using, for example, a refractometer, and to correct the refraction as outlined below.

Figure 13:
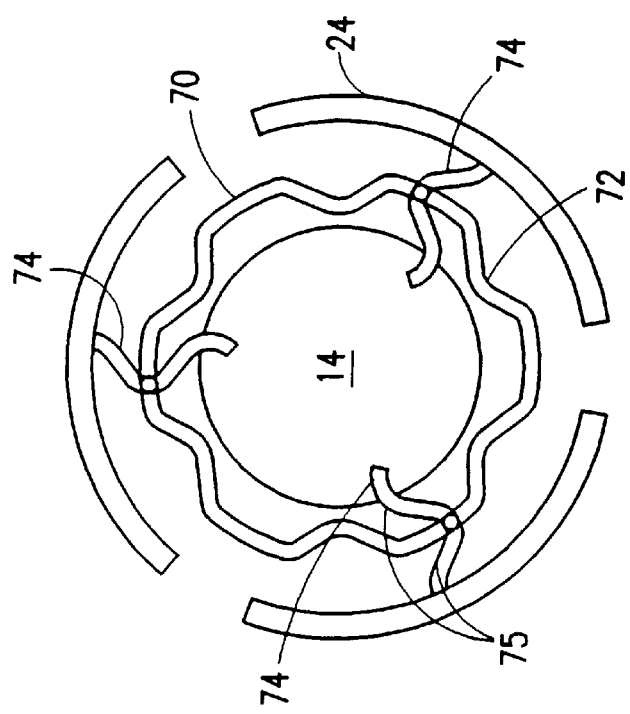
FIG. 13 is a front elevation of a modified, adjustable optic having more than two fulcrums and associated levers.

This adjustment may be accomplished by means of two alternative embodiments of the invention, which are operable either separately or together, both of which are shown schematically in FIG. 13. The first alternative embodiment, which allows adjustment of optic 14 toward posterior wall 18, makes use of a ring 70, which is formed with a plurality of kinks 72. These kinks may be straightened out during surgery so as to increase the effective diameter of the ring 70 and produce an outwardly directed radial force on linkage arms 74, whereupon there results a net movement of optic 14 toward the posterior wall.

Figure 14:
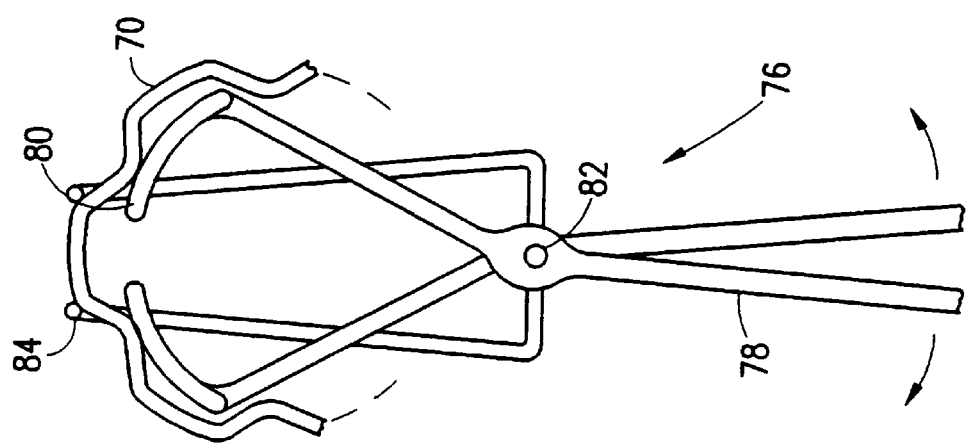
FIG. 14 is a pictorial representation of a first adjustment tool for use when implanting the intraocular lens assembly according to the invention.

FIG. 14 shows, pictorially, an adjustment tool 76 for removing, either completely or partially, kinks 72 from ring 70. Adjustment tool 76 is in the form of a pincer having a pair of handles 78 and a pair of substantially planar support members 80 opposite the handles and rotatable about a hinge axis 82. Adjustment tool 76 is inserted into the lens capsule so as to support kinks 72 on respective ones of the support members 80. Adjustment tool 76 also includes a pair of flattening members shown schematically as 84 which cooperate with support members 80 for pressing on ring 70 so that kinks 72 are flattened by flattening members 84 bearing down on support members 80.

Referring again to FIG. 13, it will be seen that as a second way of adjusting the lateral position of optic 14 in the capsule, levers 74 are also provided with two kinks 75. These kinks may be at least partially straightened using a specially designed pincer, thereby effectively lengthening the respective levers and causing a net axial movement of the optic 14 in a posterior direction toward the focal plane.

Figure 15:
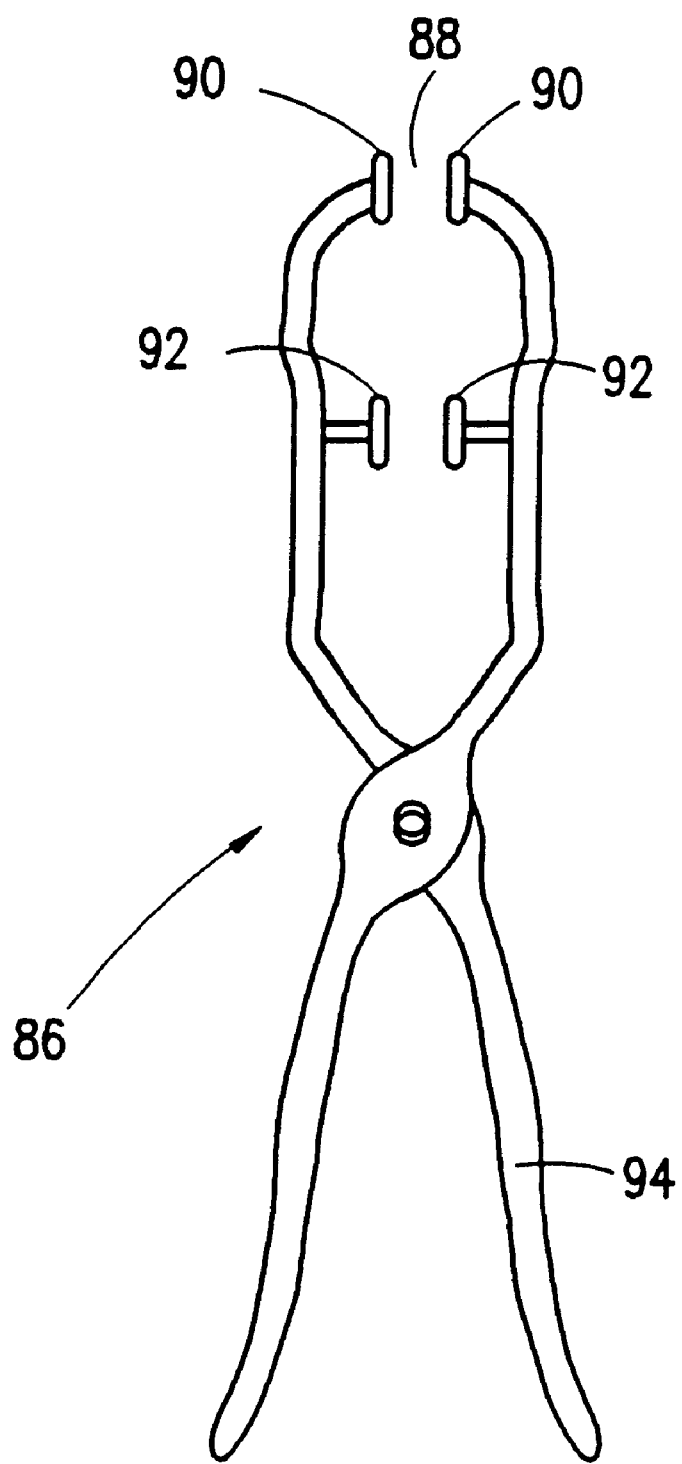
FIG. 15 is a pictorial representation of a second adjustment tool for use when implanting the intraocular lens assembly according to the invention.

Referring now to FIG. 15, a specially designed pincer for straightening out simultaneously both kinks 75 will be described. A pincer shown generally as 86 includes a head portion 88 having two upper aligned jaws 90 and two lower aligned jaws 92. In use, the two kinks 75 in the levers 74 are respectively aligned between the two pairs of jaws such that closing the jaws by means of a handle 94 flattens kinks 75, and causes the desired axial movement of the optic 14 in a posterior direction toward the focal plane.

As has been explained above, a resilient biasing force may conveniently be provided by the natural elasticity of the posterior capsule wall 18 and the edge of the lens capsule 19. In this case, for those embodiments of the invention which require the restoring force of the posterior wall on the optic, the position of the optic 14 within the lens capsule 16 must be adjusted so that, for correct far vision when the ciliary muscle is completely relaxed, the rear surface of the optic 14 contacts the posterior capsule wall 18. This too can be provided by the methodology described with respect to FIGS. 13–15.

In the preferred embodiments described hereinabove, lens assembly 12 is mounted completely within lens capsule 16 and an inward radial resilient biasing force is provided by the inherent elasticity of remaining portions of the lens capsule. However, the lens capsule may be dispensed with for some of these embodiments by providing auxiliary springs which act as tensile elements 96, as shown in FIGS. 5, so as restore the optic to its equilibrium position on relaxation of the ciliary muscle, and by attaching or anchoring the lever arms to the ciliary muscle or zonules. The inward radial biasing force may comprise, for example, a tensioned ring attached to the zonules or to the ciliary muscle itself.

The present invention has been. described, generally, for lens implants utilizing rigid optics. Alternative preferred embodiments of the above described embodiments of the invention utilize soft optics which may have a number of advantages over rigid optics. Firstly, the soft optics may be folded during implantation, such that the opening in the anterior wall of the lens capsule may be reduced. Secondly, some of the joints, for example, those which provide flexible joints at the juncture of the linkage arms and the optic or between the fulcrum and the optic, may be dispensed with and their function assumed by a slight bending of the edges of the optic itself.

In general, the materials used in the present invention are similar to those used in the prior art and include nylon and proline for the resilient linkage arms and the flexible elements, polymethylmethacrylate (PMMA) or hydrogel for the rigid optic and silicone for the soft optic. Preferably the rigid linkage arms and other rigid elements are formed of stainless steel wire optionally covered by proline or nylon or other inert material. The surface of all or part of the lens system may be covered with Haperin or other biologically active compound to reduce body rejection of the lens system.

It is to be understood that, during cataract operations, at least part of the anterior capsule wall is usually destroyed and part of the posterior capsule wall may also be damaged. Therefore, the term "posterior capsule wall" as used in the specification and claims embrace also partial capsule walls as appropriate.

I claim:

1. An intraocular lens assembly for implantation in a human eye, said eye including at least a portion of a lens capsule, a ciliary muscle and zonules controlled by the ciliary muscle, the assembly comprising:

an optic having anterior and posterior surfaces;

an at least partial ring adapted to cooperate with the ciliary muscle or the zonules; and at least two linkage elements, each being pivotably attached to the optic at a first position on the element and being pivotably attached to the at least partial ring at a second position on the element to cause axial movement of the optic in response to movement of the ciliary muscle or the zonules;

and also comprising a generally rigid ring having a diameter greater than that of the optic and less than that of said at least partial ring and wherein the linkage elements are pivotably attached at locations intermediate the ends of the linkage elements onto said rigid ring at pivots located on said rigid ring.

2. An intraocular lens assembly according to claim 1 wherein the pivots comprise flexible portions in said otherwise rigid ring.

3. An intraocular lens assembly according to claim 2, wherein:

the rigid ring is formed of at least two rigid sections interconnected by a biologically inert sleeve so as to allow twisting of respective portions of the sleeve intermediate the rigid sections, and said respective portions of the sleeve serve as fulcrums.

4. An intraocular lens assembly according to claim 3, wherein said rigid ring is provided with one or more initial kinks which can be at least partially straightened during implantation of the lens assembly in order to adjust the distance of the optic from the rear surface of the eye.

5. An intraocular lens assembly according to claim 3, wherein at least two optics are commonly coupled to the respective linkage elements.

6. An intraocular lens assembly according to claim 4, wherein at least two optics are commonly coupled to the respective linkage elements.

7. An intraocular lens assembly according to claim 2, wherein said rigid is provided with one or more initial kinks which can be at least partially straightened during implantation of the lens assembly in order to adjust the distance of the optic from the rear surface of the eye.

8. An intraocular lens assembly according to claim 7, wherein at least two optics are commonly coupled to the respective linkage elements.

9. An intraocular lens assembly according to claim 2, wherein at least two optics are commonly coupled to the respective linkage elements.

10. An intraocular lens assembly according to claim 1, wherein at least two optics are commonly coupled to the respective linkage elements.

11. An intraocular lens assembly for implantation in a human eye, said eye including at least a portion of a lens capsule, a ciliary muscle and zonules controlled by the ciliary muscle, the assembly comprising:

an optic having anterior and posterior surfaces;

an at least partial ring adapted to cooperate with the ciliary muscle or the zonules; and at least two linkage elements, each being pivotably attached to the optic at a first position on the element and being pivotably attached to the at least partial ring at a second position on the element to cause axial movement of the optic in response to movement of the ciliary muscle or the zonules;

wherein each of said linkage elements is adapted to apply a resilient bias to maintain the optic at a desired distance from the rear surface of the eye; and wherein the at least a portion of a lens capsule includes at least a peripheral edge thereof attached to the zonules and wherein the resilient bias is at least partially applied to the edge; and wherein the lens capsule also includes at least a portion of a posterior wall thereof and wherein the resilient bias is at least partially applied to the posterior wall; and wherein said at least partial ring comprises an expanding ring associated with the edge which is adapted to contact the edge of the lens capsule and position the posterior wall toward the back of the eye and away from the center of the lens capsule.

12. An intraocular lens assembly for implantation in a human eye, said eye including at least a portion of a lens capsule, a ciliary muscle and zonules controlled by the ciliary muscle, the assembly comprising:

an optic having anterior and posterior surfaces;

an at least partial ring adapted to cooperate with the ciliary muscle or the zonules; and at least two linkage elements, each being pivotably attached to the optic at a first position on the element and being pivotably attached to the at least partial ring at a second position on the element to cause axial movement of the optic in response to movement of the ciliary muscle or the zonules;

wherein each of said linkage elements is adapted to apply a resilient bias to maintain the optic at a desired distance from the rear surface of the eye; and wherein the at least a portion of a lens capsule includes at least a peripheral edge thereof attached to the zonules and wherein the resilient bias is at least partially applied to the edge; and wherein the lens capsule also includes at least a portion of a posterior wall thereof and wherein the resilient bias is at least partially applied of the posterior wall; and wherein the resilient bias is at least partially applied by stretching of the posterior capsule wall attached to the ciliary muscle at opposing extremities of the lens capsule; and wherein said at least partial ring comprises an expanding ring associated with the edge which is adapted to contact the edge of the lens capsule and position the posterior wall toward the back of the eye and away from the center of the lens capsule.

13. An intraocular lens assembly according to claim 12 wherein the rigid ring is formed of alternating rigid and elastic portions.

14. An intraocular lens assembly for implantation in a human eye, said eye including at least a portion of a lens capsule, a ciliary muscle and zonules controlled by the ciliary muscle, the assembly comprising:

an optic having anterior and posterior surfaces;

an at least partial ring adapted to cooperate with the ciliary muscle or the zonules; and at least two linkage elements, each being pivotably attached to the optic at a first position on the element and being pivotably attached to the at least partial ring at a second position on the element to cause axial movement of the optic in response to movement of the ciliary muscle or the zonules;

wherein at least a portion of the linkage elements are provided with one or more initial links which can be at least partially straightened during implantation of the lens assembly in order to adjust the distance of the optic from a rear surface of the eye.

* * * * *